United States Patent [19]
Watanabe et al.

[11] Patent Number: 6,093,571
[45] Date of Patent: Jul. 25, 2000

[54] METHOD OF GENE TRANSFER INTO POLLEN BY ION BEAM IRRADIATION

[75] Inventors: Hiroshi Watanabe; Atsushi Tanaka, both of Gunma-ken; Masayoshi Inoue, Kyoto, all of Japan

[73] Assignee: Japan Atomic Energy Research Institute, Tokyo, Japan

[21] Appl. No.: 09/201,776

[22] Filed: Dec. 1, 1998

[30] Foreign Application Priority Data

Dec. 2, 1997 [JP] Japan ................................. 9-331708

[51] Int. Cl.⁷ .......................... C12N 15/82; C12N 15/01; C12N 15/00
[52] U.S. Cl. ........................ 435/468; 435/447; 435/440
[58] Field of Search ................................. 800/278, 260; 435/468, 447, 440

[56] References Cited

U.S. PATENT DOCUMENTS 5,049,500  9/1991  Arnizen et al. ..................... 435/172.3

OTHER PUBLICATIONS

Tanaka et al., Beam Interactions with Materials & Atoms, Nuclear Instruments and Methods in Physics Research B 129, 42–48, 1997.

Potrykus, Gene Transfer to Cereals: An Assessment, Bio/Technology, pp. 535–542, 1990.

Tanaka et al., "Beam Interactions with Materials & Atoms," Nuclear Instruments and Methods in Physics Research B 129, 42–48 (1997).

*Primary Examiner*—David T. Fox
*Assistant Examiner*—Anne Marie Grünberg
*Attorney, Agent, or Firm*—Banner & Witcoff, Ltd.

[57] ABSTRACT

A specific gene or DNA can be directly transferred into the pollen of a plant by selectively irradiating the shell of the pollen with ion beams without affecting the cell nucleus and thereafter immersing the irradiated pollen in a solution containing the specific gene or DNA of interest. The shell of the pollen of a plant may be irradiated with ions having a linear energy transfer (LET) of 5–10,000 keV/$\mu$m to a controlled depth of ion injection. Hybridizing with pollen into which the specific gene or DNA has been transferred allows the specific gene to be transferred into a fertile embryo, thereby creating a transgenic plant.

1 Claim, 3 Drawing Sheets

METHOD OF GENE TRANSFER INTO POLLEN BY ION BEAM IRRADIATION

BACKGROUND OF THE INVENTION

This invention relates to a method of transferring a genetic substance directly into a plant's pollen after it is irradiated with ion beams of controlled energy to disrupt the shell of the pollen selectively so that the efficiency of transfer of a specific gene or DNA is enhanced. The method of the invention is broadly applicable to the breeding of plants.

Many techniques have been developed with a view to transferring an isolated useful gene into a plant species of interest. Such prior art techniques include: (1) a T-DNA method in which a specific gene is incorporated into a vector Ti plasmid of Agrobacterium, which is then infected to a plant to transfer the gene; (2) an electroporation method in which electric pulses are applied to a protoplast so that its cell membrane is disrupted temporarily and a gene is transferred into the cell; (3) a laser piercing method in which laser beams of a micron size is applied to a cell or tissue under examination with a microscope so that a hole is made momentarily and a gene is transferred into the cell or tissue through hole; and (4) a particle gun method in which fine metal particles of 1–3 μm in diameter that are covered with a gene or DNA are injected into a cell or tissue with compressed air or the like so that the gene or DNA is transferred into the cell or tissue.

The T-DNA method requires two steps; in the first step, a vector incorporating a specific gene is transferred into an Agrobacterium by a freeze-thaw cycle, electroporation or some other suitable method; in the next step, a plant cell or slice is infected with the bacterium. In addition, due to the low infection of monocotyledons with Agrobacterium, the use of the T-DNA method is generally limited to dicotyledons. As a further problem, some dicotyledons are difficult to transform even if they are infected with Agrobacterium and this presents a need to set strict conditions. What is more, redifferentiated individuals are not easy to grow.

The electroporation method is applicable not only to dicotyledons but also to monocotyledons. However, a protoplast has to be prepared from isolated cells and the plant species that can be treated by this method are limited because the method is only applicable to those plants for which a cultivation system has been established to enable the growing or redifferentiated individuals from a proplast into which a gene has been transferred. Another problem with the electroporation method is the low efficiency of gene transfer since many cells die upon application of electric pulses.

The laser piercing method permits efficient gene transfer not only into cells but also to tissues such as hypototyl. However, due to the need of operation under examination with a microscope, it is difficult to treat a large volume of samples by this method. In addition, the method is not applicable to samples that cannot be manipulated under microscope and breeding of redifferentiated individuals is cumbersome.

The particle gun method is effective for plant species that have difficulty with culturing protoplasts and it permits direct gene transfer into viable cells having cell wall. The method has an additional advantage of enabling treatment of a large volume of samples. On the other hand, the method has to be operated under vacuum. In addition, many cells die under the impact of fine gold or tungsten particles and it is not easy to grow re-differentiated individuals. These facts contribute to the low efficiency of gene transfer that can be achieved by the particle gun method.

The number of plants which have an established cultivation system for regenerating plants from protoplasts and so forth is comparatively small. Regeneration may be possible with experimental plants it is often impossible with cultured plants. The prior art that can be used to create transgenic plant includes the T-DNA method, the laser piercing method and the particle gun method. In the T-DNA method, the plant species that can be transformed are limited. In this respect, physical techniques that involve less constraint are desirable. However, the laser piercing method which is a physical method of gene transfer is not applicable to samples that cannot be examined under microscope and it has an additional disadvantage of being incapable of treating a large volume of samples. In this respect, the particle gun method which is another physical technique is preferred.

Under the circumstances, the particle gun method is currently used widely for the purpose of transferring specific genes. In fact, however, many cells die under the great physical impact imposed by the particle gun method or on account of the vacuum under which the treatment is done. In addition, growing redifferentiated individuals is not easy. As a result, the efficiency of gene transfer is lowered. In order to solve these problems, a technique has to be developed that is capable of transferring a gene without causing significant damage to the cell nucleus.

If a specific gene can be transferred into a pollen grain, subsequent hybridization with the gene carrying pollen will permit gene transfer into fertile embryo, thus leading to the preparation of a pollen serving as a kind of vector. However, the shell of the pollen is strong both chemically and physically and cannot be removed by any of the prior art methods. Hence, it has been difficult to transfer a specific gene into the pollen.

SUMMARY OF THE INVENTION

Ion beams are characterized by their ability to impart huge energy to a specific site and the depth of their injection into the site can be controlled by adjusting their energy. The present invention provides a method of transferring a specific gene or DNA into pollen cells efficiently by making use of these characteristics of ion beams. In the method, a pollen grain is irradiated with an ion beam to disrupt its shell selectively so that the efficiency of transfer of the gene or DNA is enhanced to permit efficient gene or DNA transfer. The present invention also provides details of an irradiation apparatus that is used to implement the method.

In the course of their study to solve the aforementioned problems of the prior art, the present inventors particularly noted the application of ion beams as a method capable of selectively disrupting the shell of pollen without damaging the cell nucleus. Ion beams have the following two advantages, for which the inventors selected them as an effective means of attaining the stated object: ion beams have higher LET (linear energy transfer) than electron beams, X-rays and other radiations and can impart high energy to a specific site and, hence, are expected to have a high capability of disrupting the shell structure of pollen; the depth of injection of ions into pollen can be controlled by adjusting the energy of the ion beams being applied.

With a view to attaining the stated object of the present invention, the inventors designed and set up a test ion beam applicator and conducted intensive studies using the apparatus. As a result, it was found that using the apparatus, the application of ion beams could be controlled over a depth range of 1–35 μm. An irradiation experiment in which pollen grains were irradiated with ion beams at controlled depths of ion injection revealed that not only the simple electronic energy transfer but also the energy of collision between the ions and the constituent elements of the pollen shell contributed to an efficient disruption of the shell structure. It was also found that the irradiated pollen grains had a higher DNA uptake than non-irradiated grains, thus allowing for efficient transfer of a specific gene.

DETAILED DESCRIPTION OF THE INVENTION

The ion beams to be used in the present invention may be any of the beams produced by accelerating the ions of elements ranging from hydrogen to lead that are easy to accelerate by the state-of-the-art technology. The energy of the beams to be applied is determined by the depth of ion injection that is effective in disrupting the shell of pollen and transferring a specific gene or DNA into the pollen cell. If the thickness of the shell of pollen is known, satisfactory results are attainable by using an ion beam having an insufficient flight to affect the cell nucleus. For irradiating a sample in air atmosphere, the ion beams to be applied must be transferred from vacuum into the air atmosphere through a thin film; hence, the initial energy of the beam must be selected at a value that allows for the attenuation of the ion energy in the thin film. For irradiation in vacuum, a suitable depth of injection may be attained by adjusting the initial energy of the ion beams in a vacuum chamber.

The required dose of irradiation is determined by the sensitivity of the structure of the shell of pollen to the applied ion beams. For irradiating a dry pollen grain, an optimal dose must be determined with 1 kGy taken as a guide. When irradiating pollen grains adhering to a plant, a suitable dose is desirably determined with the range of 1–100 Gy taken as a guide since they are more radiation-sensitive than dry pollen.

The LET for ion beams may be selected from the range of 5–10,000 keV/μm; however, if the ion beams are to be transferred into air atmosphere, the attenuation of energy in both a thin film and the air atmosphere must be allowed for.

The present invention will now be described with reference to the following examples using the pollen of tobacco (*Nicotiana tabacum* L, cv. BY-4). Pollen varies in size and shell thickness depending on the origin but it is essentially composed of an outer wall containing sporopollenine and cellulose and an inner wall containing pectin and cellulose. In addition, the basic intended function of ion beams is destroying the structure of organic matter by energy transfer to it. Hence, the scope of the present invention is in no way limited to the following examples using the pollen of tobacco.

EXAMPLE 1

Figure 1:
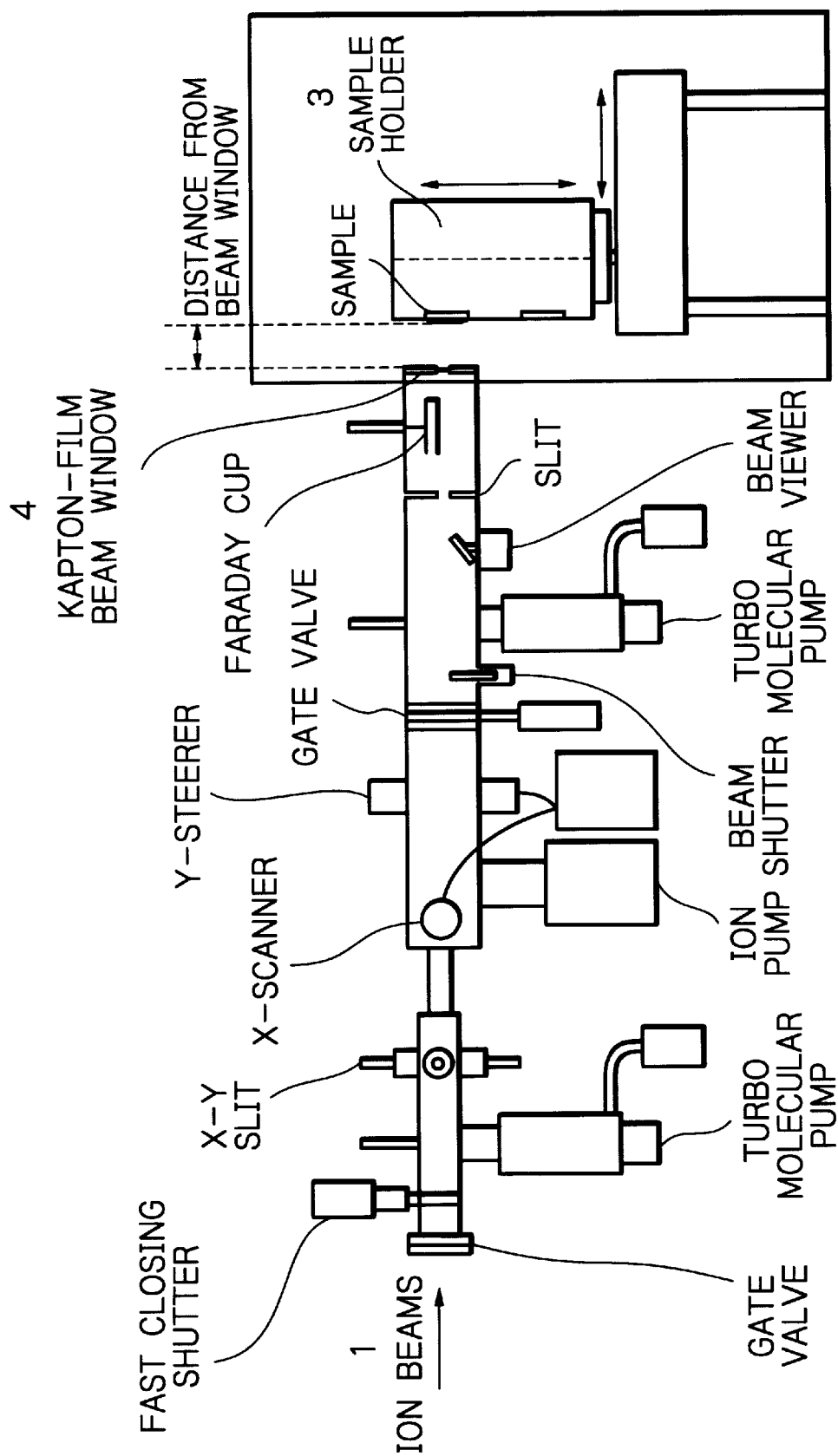
FIG. 1 is a schematic of an experimental setup for irradiating pollen with ion beams at controlled depths using the method of the present invention.

The apparatus shown in FIG. 1 is a depth-controlled cell irradiation setup the present inventors fabricated in the course of their study to develop an effective way to transfer a gene into plants. The apparatus was connected to 3 MV tandem accelerator. An accelerated ion beam 1 was scanned to a width of 10 cm and transferred into air atmosphere through a radiation-resistant polymeric (Kapton) film (8 μm thick). An organism sample 2 was fixed on a holder 3 in the form of a hexagonal column. The distance between the holder 3 and the beam window 4 in the Kapton film was variable to a precision of 1 mm.

The energy of ion beams can be adjusted by changing the initial energy of the beam with the position of the sample holder fixed or changing the distance from the beam window to the sample holder with the beam's initial energy fixed. For fine adjustment, the second method is more suitable.

Figure 2:
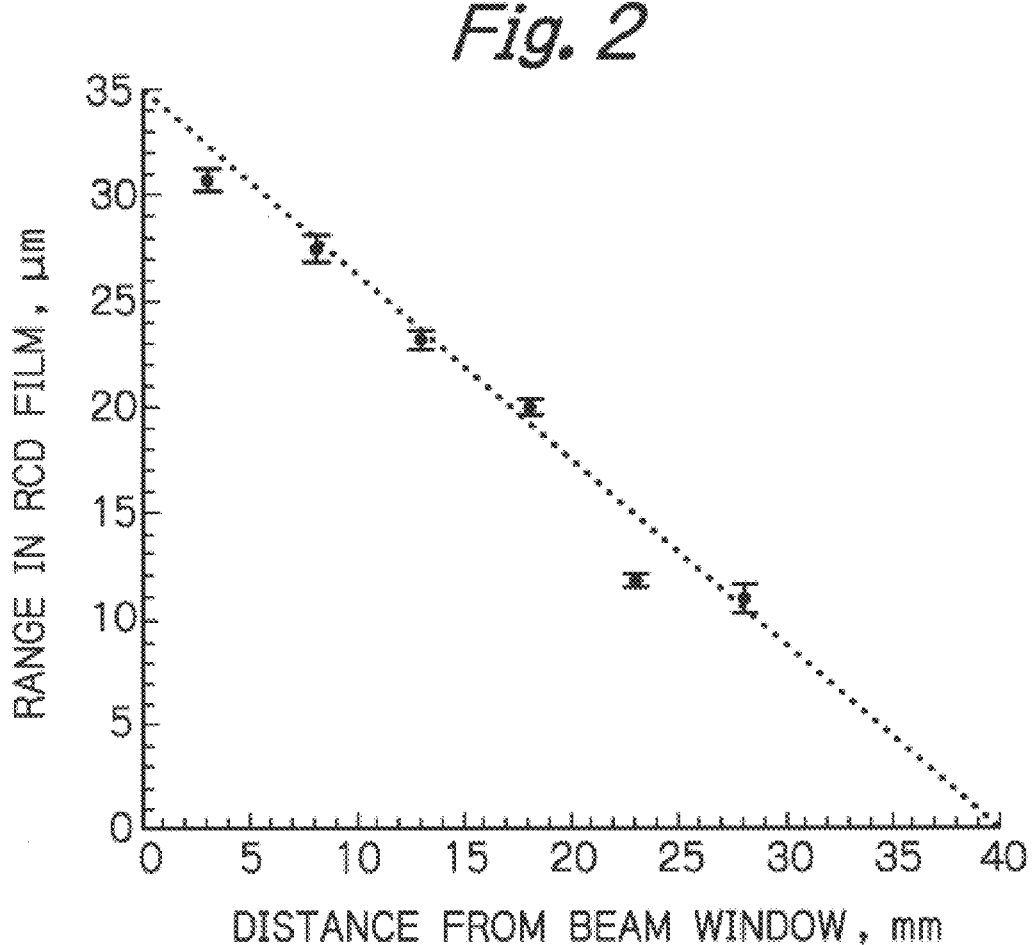
FIG. 2 is a graph showing the relation between the depth of He ion beam injection at 6 MeV and the distance from beam window.

Using the apparatus of FIG. 1 having the performance stated above, He ions of 6 MeV were transferred into air atmosphere, with the position of the sample holder being varied. The change in the flight of the ions as a function of the distance from the irradiation window is shown in FIG. 2. Obviously, the depth of ion injection decreased linearly with the distance from the beam window, reading zero at about 40 mm which was the end of the He ion flight in air atmosphere. Thus, it can be seen that under the conditions used in the experiment, the depth of ion injection could be controlled down to 35 μm by changing the distance from the beam window. The ultimate depth is variable with ion species because different ions have different initial energies. However, the behavior is the same and as in the case of the He ions shown in FIG. 2, the depth of injection decreases linearly with the increasing distance from the beam window.

EXAMPLE 2

Figure 3:
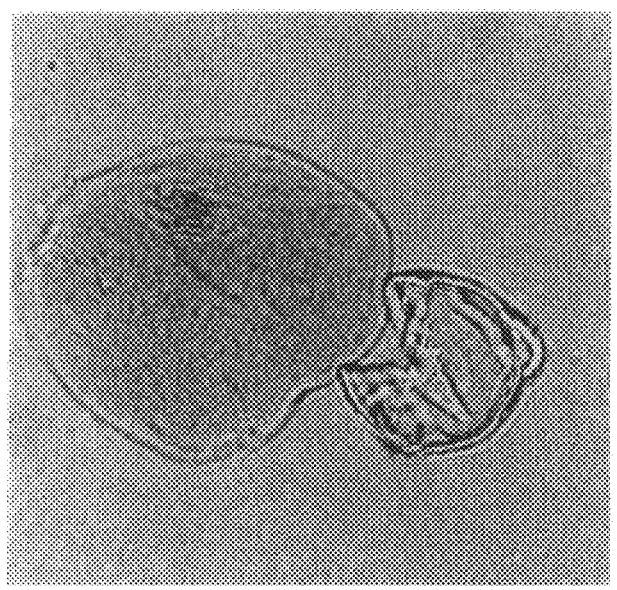
FIG. 3 is a photo showing the leakage of the pollen of *Nicotiana tabacum* L, cv. BY-4 as observed upon exposure to He ion beams.
Figure 4:
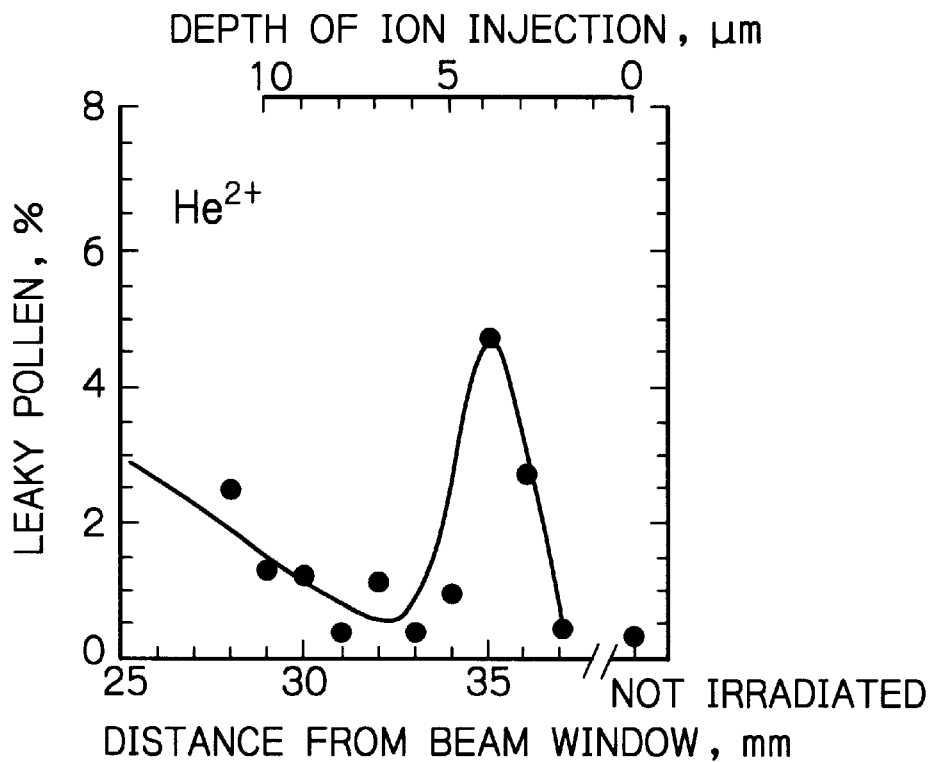
FIG. 4 shows graphically the frequency of the leakage of pollen upon depth-controlled exposure to He and C ions.
Figure 4:
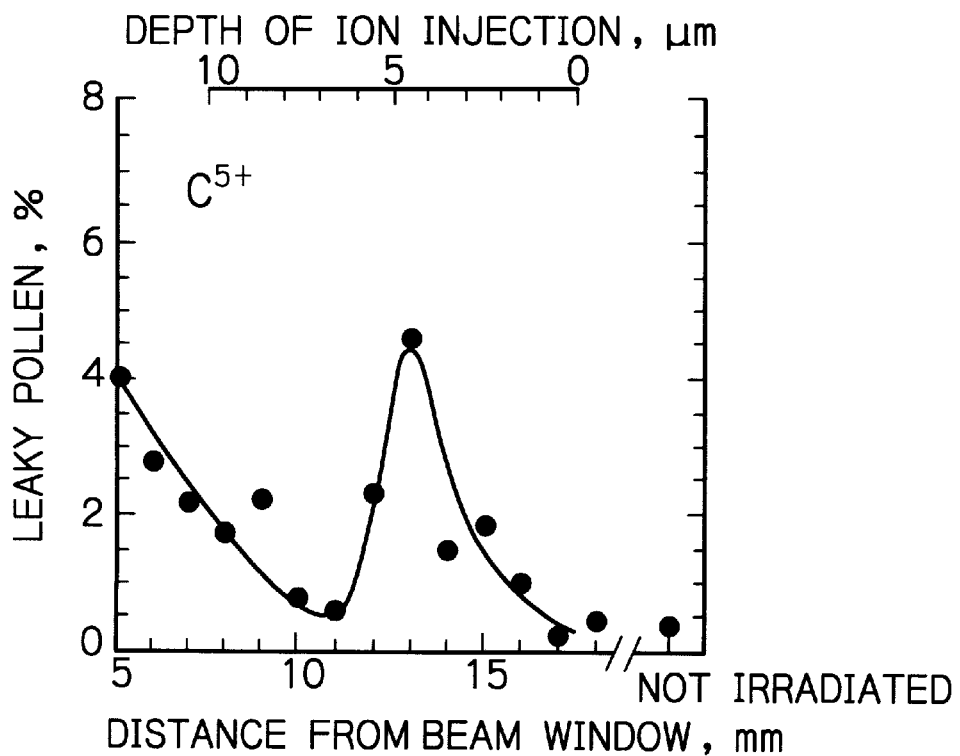

Fully ripened pollen grains of a cultured tobacco species *Nicotiana tabacum* L, cv. BY-4 were laid in a single layer and irradiated with He ion beams at 6 MeV (LET=180 keV/μm). The irradiated pollen grains were immersed in a solution of accetocarmine, whereupon the shell of the pollen ruptured and the pollen cell leaked out (see FIG. 3). This phenomenon does not occur upon exposure to other radiations and is unique to the selective disruption of the shell of pollen by exposure to ion beams at controlled depths. To evaluate the frequency of such leaky pollen at varying depths of ion injection, an experiment was conducted with the distance from the beam window varied. The result is shown FIG. 4 (see upper graph). Obviously, the shell of pollen could be ruptured most easily by injecting the ions to a depth of 4 μm.

When the ion species was changed to C ions of 18 MeV (LET=670 keV/μm), the shell of pollen was also most easily rupturable upon injecting the C ions to the same depth as in the case of He ions. Hence the selective disruption of the shell of pollen was found to be independent of ion species and LET. The energy of ion beams is not only conferred at the highest dose to the shell of pollen; at the same, the collision between the ions and the constituent elements of the shell contributes to the site-specific disruption of the shell. This is a unique effect of ion beams that cannot be achieved by any ordinary methods including enzymatic treatment.

EXAMPLE 3

Pollen grains were irradiated with He ions of 6 MeV to a depth of 4 μm as in Example 2. The thus irradiated pollen was immersed in a DNA solution (50 μg/ml) for 1 h. The result is shown in Table 1, from which one can see that the frequency of expression of the GUS gene (as contained in DNA) in the irradiated pollen was more than 4 times as high as in the nonirradiated pollen. However, the DNA uptake decreased when the depth of ion injection was less than 4 μm. Thus, irradiating the shell of pollen with ion beams to a specified depth is indispensable for effective DNA transfer. This effect was also observed with C ions.

TABLE 1

Frequency of Expression of GUS gene in Pollen Irradiated with Ion Beams at Controlled Depths

| Ion species | Fluence, (p/cm$^2$) | Not irradiated | Depth of ion injection | | |
|---|---|---|---|---|---|
| | | | 2 μm | 3 μm | 4 μm |
| He | 4 × 10$^9$ | 7.1 ± 1.9% | 13.5 ± 2.7% | 12.6 ± 3.2% | 30.9 ± 3.2% |
| C | 4 × 10$^9$ | 7.1 ± 1.9% | 11.7 ± 3.8% | 13.8 ± 2.5% | 32.1 ± 3.5% |

EXAMPLE 4

*Nicotiana tabacum* L, cv. BY-4 was pollinated with pollen into which a hygromycin-resistant gene had been transferred under the same conditions as in Example 3. As the result of this hybridization, the incidence of seed formation per sheath decreased to 26% of the value attained from the nonirradiated pollen. However, 93% of the seeds obtained could germinate. Half a percent of the seeds could germinate on a hygromycin-containing medium to form plants. Thus, the gene transferred into pollen by the method of the present invention was used in hybridization to produce seeds, which could germinate and grow to plants, in which the transferred gene was found to have been expressed.

According to the present invention, the shell of pollen is selectively irradiated with ion beams at controlled energy, whereupon the structure of the shell is disrupted selectively and effectively to enhance the transfer of a specific gene or DNA into the pollen. This enables the specific gene or DNA to be directly transferred into the pollen irrespective of the plant type of the pollen. Since the shell of pollen is difficult to remove by ordinary methods such as enzymatic treatment, irradiation with an ion beams at controlled depths is particularly effective. Pollen treated by the method of the present invention can be used as a vector for gene transfer into plants.

What is claimed is:

1. A method of transferring a specific gene or DNA directly into the pollen of a plant, the method comprising the steps of irradiating the shell of a pollen grain with ion beams without affecting the cell nucleus by adjusting the energy of the ion beams and controlling the depth of ion injection, thereby selectively disrupting the shell structure of the pollen grain so that the gene or DNA is transferred into the pollen, and thereafter immersing the irradiated pollen grain in a solution containing a specific gene or DNA of interest to transfer the specific gene or DNA into the pollen, wherein the ion beams have a linear energy transfer of 180–670 KeV/μm and wherein the depth of ion injection is from 1–35 μm.

* * * * *